(12) United States Patent
Epperson

(10) Patent No.: US 8,152,763 B2
(45) Date of Patent: Apr. 10, 2012

(54) DISPOSABLE CARPULE FOR HYPODERMIC SYRINGE

(76) Inventor: Frank E. Epperson, Aurora, CO (US)

(*) Notice: Subject to any disclaimer, the term of this patent is extended or adjusted under 35 U.S.C. 154(b) by 41 days.

(21) Appl. No.: 12/622,321

(22) Filed: Nov. 19, 2009

(65) Prior Publication Data

US 2011/0118665 A1 May 19, 2011

(51) Int. Cl.
*A61M 5/00* (2006.01)
*A61M 5/28* (2006.01)
*A61M 5/20* (2006.01)

(52) U.S. Cl. ........ 604/110; 604/135; 604/232; 604/203; 604/134

(58) Field of Classification Search ............. 604/38, 604/117, 187, 195, 241, 134, 135, 200, 203, 604/218, 232
See application file for complete search history.

(56) References Cited

U.S. PATENT DOCUMENTS

| | | | |
|---|---|---|---|
| 4,072,149 A * | 2/1978 | Tischlinger | 604/202 |
| 4,273,123 A * | 6/1981 | Lemelson | 604/110 |
| 4,804,370 A | 2/1989 | Haber et al. | |
| 4,919,657 A | 4/1990 | Haber et al. | |
| 4,986,813 A | 1/1991 | Blake, III et al. | |
| 5,061,249 A | 10/1991 | Campbell | |
| 5,104,378 A | 4/1992 | Haber et al. | |
| 5,215,533 A | 6/1993 | Robb | |
| 5,242,402 A | 9/1993 | Chen | |
| 5,328,475 A | 7/1994 | Chen | |
| 5,562,629 A | 10/1996 | Haughton et al. | |
| 5,593,391 A * | 1/1997 | Stanners | 604/232 |
| 5,931,813 A | 8/1999 | Liu | |
| 6,248,094 B1 * | 6/2001 | Epperson | 604/195 |
| 6,409,703 B1 | 6/2002 | Lu | |
| 6,530,903 B2 | 3/2003 | Wang et al. | |
| 7,513,887 B2 | 4/2009 | Halseth et al. | |

FOREIGN PATENT DOCUMENTS

JP 10099433 4/1998

* cited by examiner

*Primary Examiner* — Jackie Ho
*Assistant Examiner* — Leah Stohr
(74) *Attorney, Agent, or Firm* — The Reilly Intellectual Property Law Firm, P.C.; John E. Reilly; Ellen Reilly

(57) ABSTRACT

A standard dental syringe is made up of an outer cylinder with a plunger at one end, and a carpule which contains liquid medication to be injected into a patient is replaceably positioned within the barrel and includes a needle slidably mounted at one end of the carpule in communication with the fluid medication which is contained in a fluid chamber sealed off at each end by a plug so that when the plunger is advanced into engagement with a first plug at one end of the carpule the liquid medication is delivered through the needle and upon completion of the plunger stroke, a barbed extension of the slidable first plug member will move into engagement with the needle-retaining second plug member so that upon retraction of the plunger the needle-retaining plug member will be retracted along with the slidable first plug member. The needle is guided through a funnel-shaped sleeve assembly at the end of the barrel so that following the injection procedure the needle can be retracted and the portion of the guide can be removed so that the entire exposed end of the needle can be cut off following which both of the plug members and remainder of the needle can be once again retracted into the carpule assembly and removed from the barrel and replaced by a new carpule assembly.

9 Claims, 5 Drawing Sheets

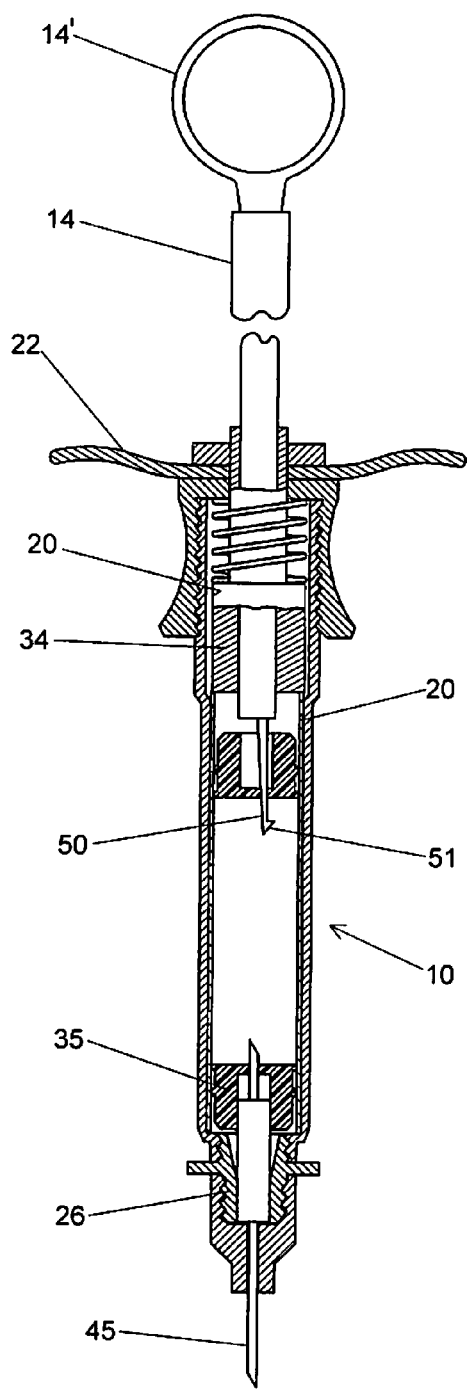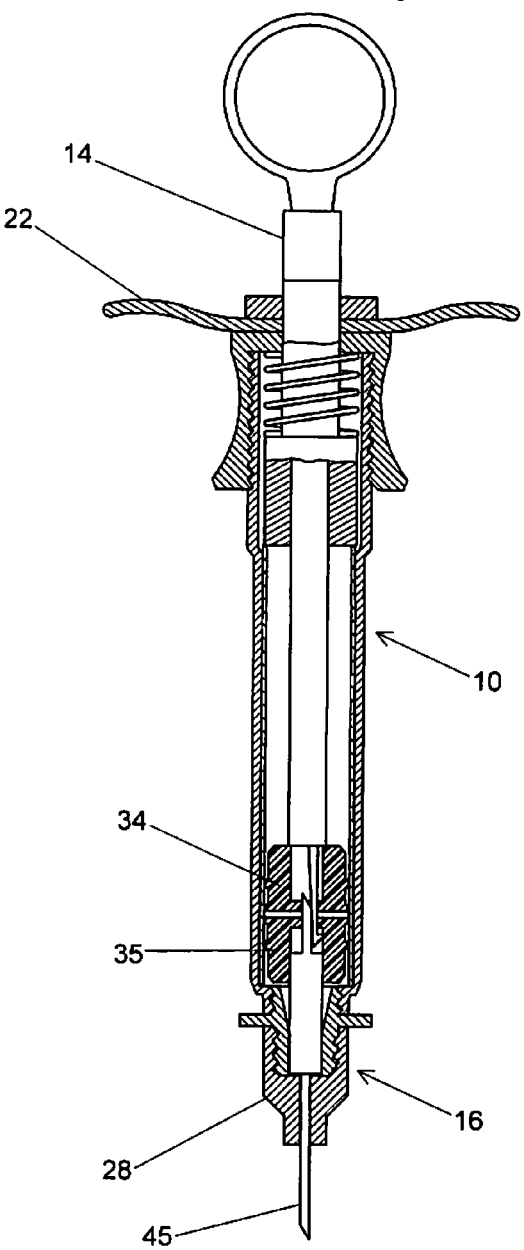

FIGURE 4
FIGURE 5
FIGURE 6
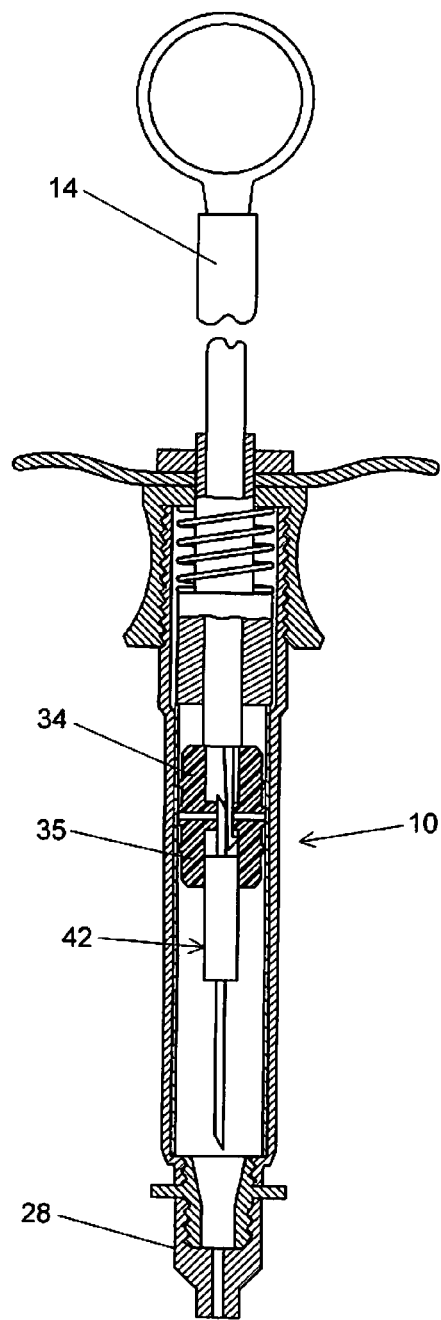
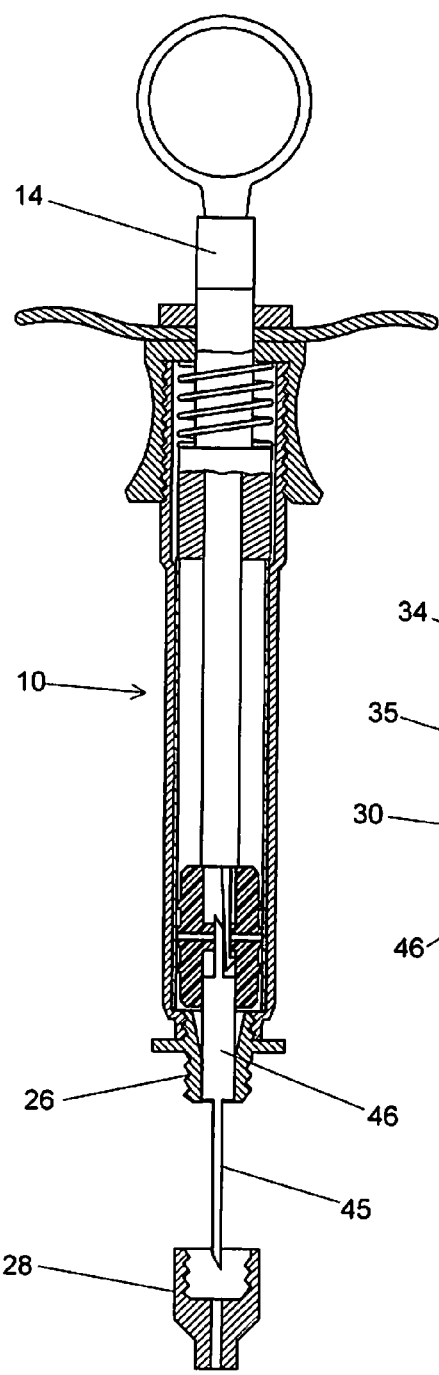
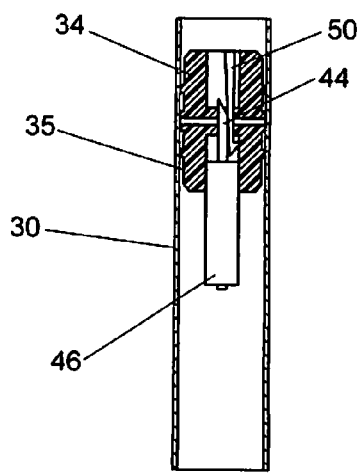

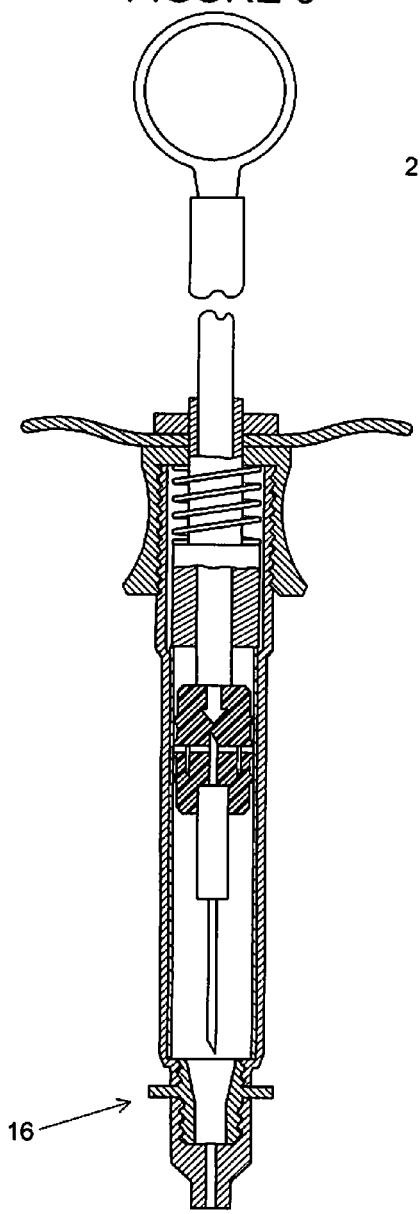
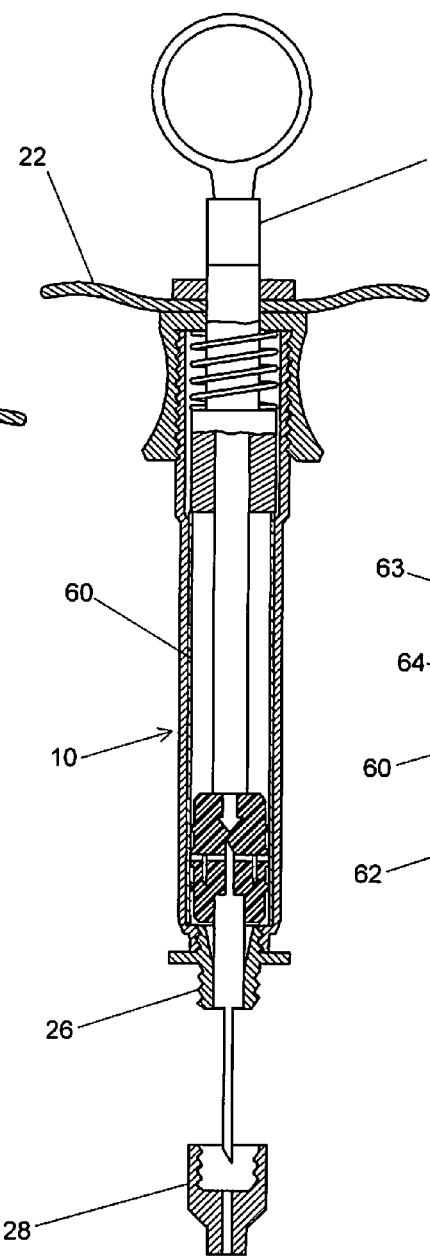
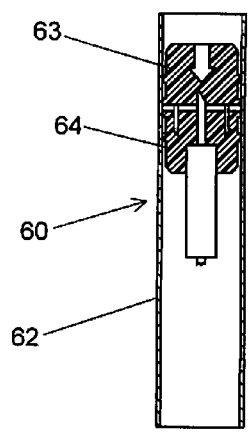
FIGURE 9
FIGURE 10
FIGURE 11

DISPOSABLE CARPULE FOR HYPODERMIC SYRINGE

BACKGROUND AND FIELD

The following relates to hypodermic syringes, and more particularly relates to a dental syringe utilizing disposable carpule assemblies of the type in which the hypodermic needle can be destroyed after use so as to prevent its reuse, such as, for example, by drug abusers.

I previously devised a dental syringe utilizing a disposable carpule in which the hypodermic needle can be completely retracted into the carpule after use and thereby allow an operator to dispose of the carpule and needle without coming into direct contact with the needle. Reference is made to my U.S. Pat. No. 6,248,094. As noted in my patent, other syringes have been devised with a single-use, disposable syringe having a fluid containment system which complements the respective retractable needle assembly. Even so, there continues to be a need, particularly in the dental field, for a retractable needle assembly in which the injectable end of the needle can be completely destroyed prior to retraction into the carpule assembly after its use and in this way prevent cross-contamination or other accidental injury to the operator when delivering an injectable solution to a patient. For example, in accordance with my '094 patent, the needle assembly can be fully retracted into the carpule following use and the one end of the needle opposite to the injectable end can be at least partially destroyed but in doing so moves the needle assembly out of alignment with the exit end of the syringe so that it cannot be extended again through the opening without considerable trial and error; and even then cannot be fully extended so as to be accessible for complete destruction or severance of the injection end from the rest of the needle assembly. Still further, after destruction, it is desirable to once again be able to retract the remainder of the needle assembly into the carpule and remove from the syringe for disposal. In this relation, there is also a need for a guide assembly at the end of the syringe in which a portion of the guide can be removed after the needle injection and retraction into the carpule which will enable maximum exposure of the injection end of the needle when it is once again extended from the carpule assembly for destruction.

SUMMARY

A foremost object is to provide a method and apparatus for advancing a needle through a guide at the end of a syringe to an extended position for injecting a medical solution into a patient, retracting the needle into the syringe followed by once again extending the needle through the guide to permit destruction of the end of the needle and thereafter retracting the remainder of the needle back into the syringe; and further characterized by removing a portion of the guide member at the end of the syringe after the injection to expose a greater portion of the needle for destruction.

It is therefore desirable to provide for an improved guide member in combination with a standard syringe housing and plunger which are familiar to the operator in combination with a disposable carpule containing an injectable solution and which enables repeated extension of the needle assembly for injection and subsequent destruction.

Another feature is to provide for a carpule assembly of the type described in which the needle can be exposed to different lengths beyond the end of the syringe so as to assure complete removal and destruction of the operating end of the needle.

Still another feature is to provide for a carpule having a fluid-expelling plug member at one end and a needle-retaining plug member at the opposite end which define a fluid chamber therebetween, one end of a standard hypodermic needle extending centrally through the needle-retaining member into communication with the fluid chamber, and the fluid-expelling plug member has a generally hook-like extension in off-center relation to the needle so that at the end of its forward travel will move into engagement with the needle-retaining member without deflecting the needle, and in this way the needle can be repeatedly advanced and retracted through the needle guide at the end of the syringe. A related feature is to provide a needle guide in which a portion of the needle guide can be removed after injection and the needle once again advanced through the remaining inner concentric portion of the guide in order to expose substantially the entire injection end of the needle to enable it to be cut off, and the reminder of the needle along with the plug members can be fully retracted into the carpule.

In the first embodiment, a syringe is comprised of a syringe having a cylinder and plunger at a trailing end, a carpule defining a fluid chamber for medication removably positioned in said cylinder having a retractable needle at a trailing end of said carpule for extension between a retracted position within said carpule and an extended position beyond a leading end of said syringe opposite to said plunger; and a generally funnel-shaped guide member at said trailing end of said syringe for guiding advancement of said needle between the retracted and extended positions.

In a second embodiment, a plurality of barbs are provided in place of a central spire point to effect engagement between the plug members. In both embodiments, a hub is affixed to a flange at the leading end of the barrel and the hub being funnel-shaped to guide the needle through the hub as well as through an outer concentric guide member which is threaded onto the hub. In this way, after the needle has been retracted after injecting the medication, the outer guide can be removed from the hub and the needle once again advanced through the hub so that the entire injection end of the needle is exposed for removal and destruction.

The above and other objects and advantages will become more readily understood from a consideration of the following detailed description of the embodiments when taken together with the accompanying drawings in which:

BRIEF DESCRIPTION OF THE DRAWINGS

FIG. 2 is a longitudinal section view of the first embodiment shown in a position at rest prior to injection;

FIG. 3 is a longitudinal section view of the embodiment shown in FIGS. 1 and 2 at the completion of injection;

FIG. 4 is a longitudinal section view of the embodiment shown in FIGS. 1 to 3 with the needle in a retracted position following injection;

FIG. 5 is a longitudinal section view of the first embodiment shown with a portion of the front guide removed and the needle in an extended position;

FIG. 6 is a sectional view of the carpule assembly of the first embodiment with the remainder of the needle assembly retracted following removal of the injection end of the needle;

FIG. 9 is a longitudinal section view of the second embodiment with the needle assembly shown in the retracted position following injection;

FIG. 10 is a longitudinal section view of the second embodiment with the needle shown in an extended position after removal of a portion of the guide member; and FIG. 11 is a longitudinal section view of the modified form of carpule assembly after removal of the injection end of the needle and separation of the carpule assembly from the syringe.

DETAILED DESCRIPTION OF FIRST EMBODIMENT

Figure 1:
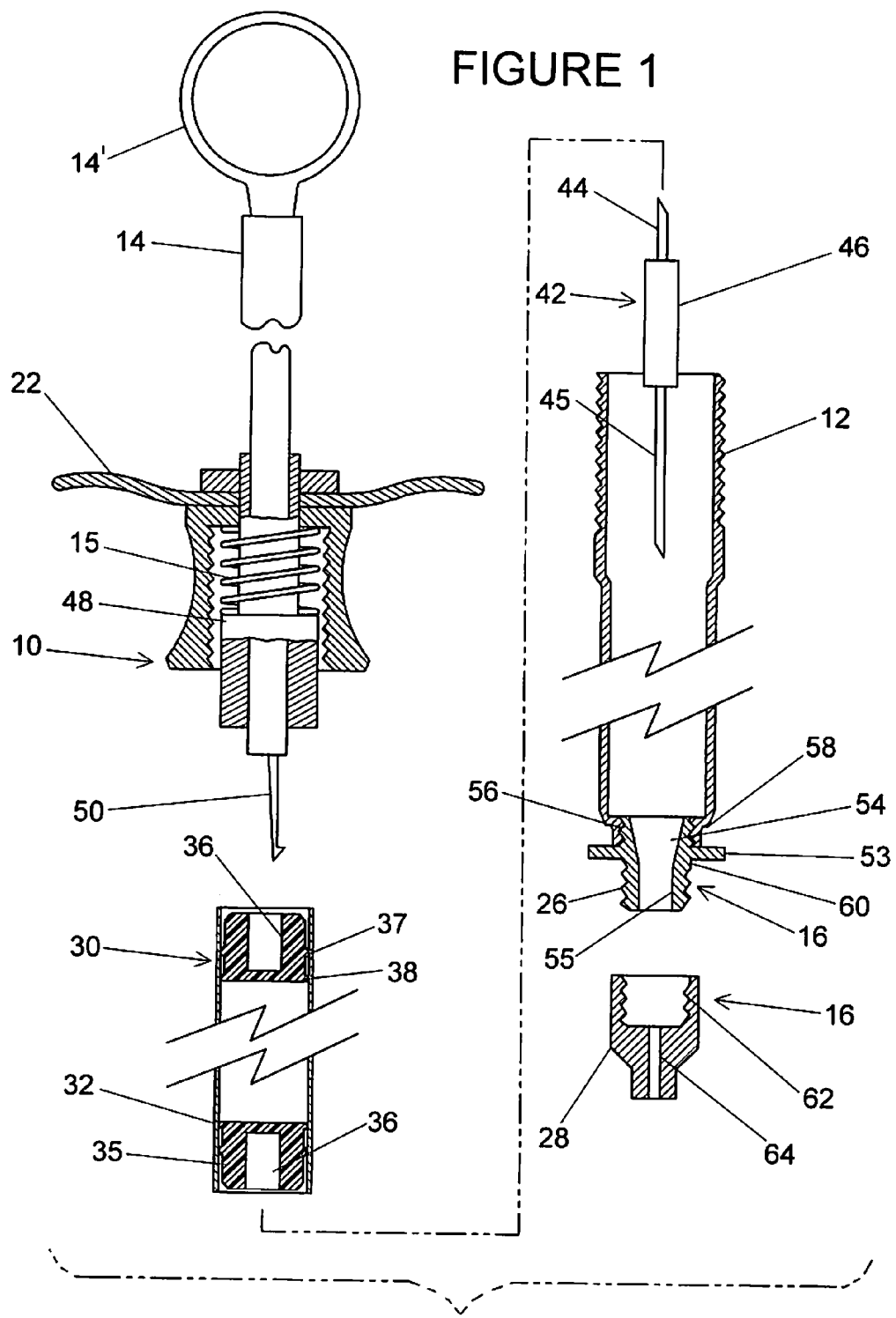
FIG. 1 is an exploded view of the first embodiment of a hypodermic syringe.

FIGS. 1 to 6 illustrate a hypodermic syringe which is made up of an elongated cylindrical barrel 12 having a spring-loaded plunger 14 with a ring-like gripping end 14' at one end and a needle guide 16 at the opposite end of the barrel. The syringe 10 is of the type utilized in dentistry to administer anesthetics, the barrel 12 having diametrically opposed, elongated recessed portions 20 and a finger grip 22 at the one end which receives the plunger 14. The needle guide or hub 16 at the opposite end is modified for a purpose to be described and is broadly made up of an inner hub 26 and an outer sleeve 28 which is threadedly connected to the hub.

As best seen from the exploded view of FIG. 1, a carpule assembly 30 is in the form of an elongated tube 32 which is composed of clear plastic or glass having an external diameter conforming to the inner reduced diameter at the leading end of the barrel 12, and a medication in the form of an injectable solution is retained in the tube by first and second plug members 34 and 35 at opposite ends of the tube 32. The plugs are of corresponding size and are composed of a resilient material, such as, rubber or plastic, each of the plugs 34 and 35 including a counterbore 36 and spaced annular ridges 37 and 38. The plugs 34 and 35 are slidable within the tube 32 in a manner to be described and are retained against movement beyond the opposite ends of the tube 32 by inturned edges 39 and 40.

A hypodermic needle or cannula 42 has opposite pointed ends 44 and 45 of a continuous length and affixed within an intermediate surrounding collar portion 46 in a conventional manner. The pointed end 44 extends through the plug 35 into communication with the liquid-filled chamber within the carpule, and the relatively long injection or leading end 45 of the needle normally projects through the guide assembly 16 for the purpose of injecting the medication into a patient. In this relation, the plug 35 serves as the needle-retaining plug member and the plug 34 serves as the fluid-expelling member. Specifically, the plug members 34 and 35 are slightly undersized with respect to the carpule tube 32 but undergo slight expansion when the end of the plunger is advanced through the fluid-expelling plug member 34 with the collar 46 on the needle assembly 42 extending through the counterbore in the plug member 35, and the convex ridges 37 and 38 will assist in maintaining a sealed engagement between the plug members 35, 36 and the tube 32.

The plunger 14, which is of conventional construction, extends through the rearward or trailing end of the syringe 10 and is spring-loaded by a compression spring 15 interposed between the finger grip 22 and a seat 48 at the end of the barrel 12. When the ring-like gripping end 14' of the plunger is grasped to advance the plunger forwardly it will cause a spire point 50 at its leading end to advance through the counterbore 36 in slightly offset relation to center and at the same time force the plug 34 forwardly through the carpule to expel the medication through the needle 42, as best seen from the sequential movement of the plunger as shown in FIGS. 2 and 3. Thus at the end of the forward movement of the plug 34 into abutting relation to the plug 35 the spire point 50 will penetrate the plug 35 and advance alongside the inner end 44 of the needle and, with its barbed end 51, will become anchored against accidental release within the plug 35. In this way, the plugs will be effectively joined together along with the needle assembly 42 and retracted as one unit through the carpule tube in response to withdrawal of the plunger 14 as shown in FIG. 4. Accordingly, it is important to understand that the needle assembly 16 will not be deflected or bent by the spire point 50 so that the leading end 45 of the needle will maintain its aligned relationship with the guide assembly 16. Specifically, the inner concentric portion 26 of the guide assembly has a funnel-shaped bore 54 which converges into a straight cylindrical bore portion 55 having an internal diameter corresponding to the external diameter of the collar 46 of the needle assembly; and the hub is externally threaded at 56 for threaded connection to a reduced, internally threaded end 58 of the barrel 12. In turn, an externally threaded portion 60 of the cylindrical end 55 threadedly receives internally threaded end 62 of the outer concentric guide portion 28, the latter being advanced over the inner concentric portion until it seats firmly against an external flange 53 on the hub 26. The internally threaded counterbore 62 merges into a counterbore 64 of substantially reduced diameter to receive and support the leading end 45 of the needle assembly 46 for the injection step.

In order to prevent re-use of the needle as well as accidental injury to persons coming into contact with the carpule assembly, as shown in FIG. 5, in order to dispose of the leading end 45 of the needle 42 up to the end of the collar 46, the outer guide portion 28 is unthreaded from the inner guide portion 26, as illustrated in FIG. 5, so that the entire leading end 45 is exposed beyond the end of the guide portion 26 and can be severed at its junction with the collar 46 followed by retraction of the remainder of the needle 42 into the carpule assembly 30 as shown in FIG. 6. In this regard, the needle end 45 can be clipped off or destroyed by any one of a number of well known procedures which typically involves slicing into a number of segments within a disposal chamber.

FIG. 6 illustrates the carpule assembly after removal from the barrel through one of the recessed portions in the wall of the barrel 12 with the shorter needle end 44 completely embedded within the plug members along with the spire point 50, and a new disposable carpule assembly 30 is positioned within the barrel 12.

DETAILED DESCRIPTION OF SECOND EMBODIMENT

Figure 7:
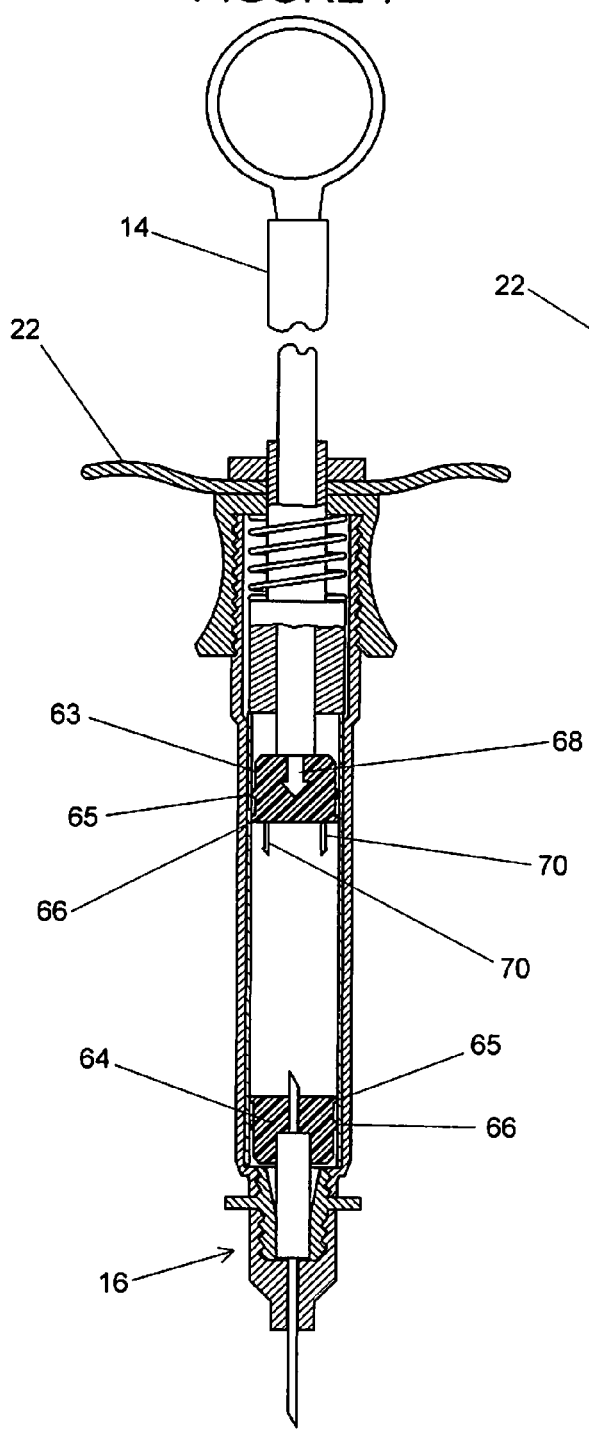
FIG. 7 is a longitudinal section view of a second embodiment having a modified form of carpule assembly for a standard syringe.
Figure 8:
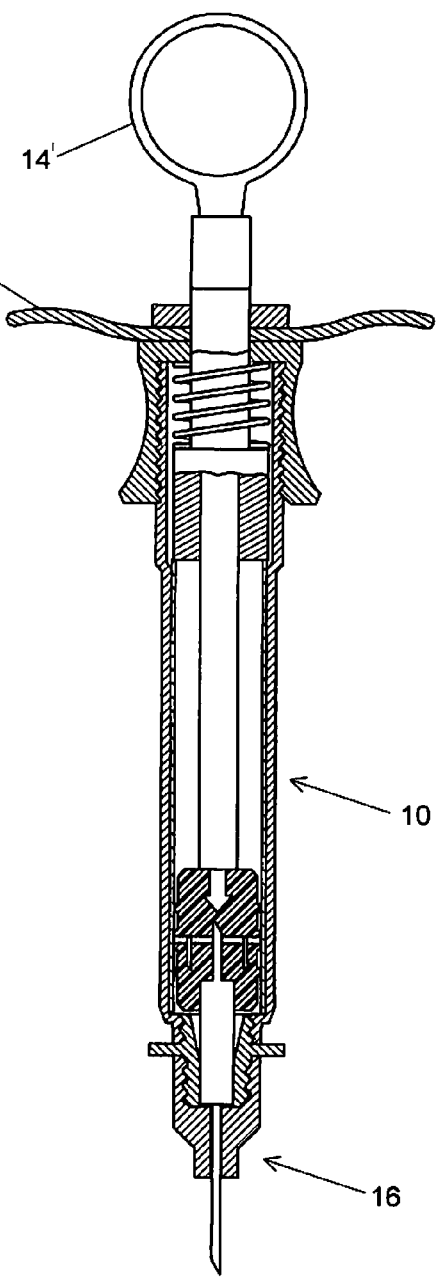
FIG. 8 is a longitudinal section view of the second embodiment with the needle in the extended position.

In FIGS. 7 through 11, a second embodiment for achieving complete removal and/or destruction of the leading end 45 of a needle assembly 42 is shown and wherein like parts are designated by corresponding numerals. The operation is the same as that of the first embodiment and broadly comprises the steps of advancing a needle 42 through a guide 16 at the end of a syringe 10 to an extended position for injecting a medical solution into a patient, retracting the needle assembly 42 into the syringe 10 followed by once again extending the needle end 45 through the guide 16 to permit destruction of the leading end 45 of the needle and thereafter retracting the remainder of the needle back into the syringe 10. Once again, a disposable carpule assembly 60 is removably inserted within the barrel 12 and is seated against the leading end of the barrel 12 by a spring-loaded plunger 14, the needle assembly 42 projecting from the barrel 12 with the collar 46 inserted into the inner hub 26 of the guide assembly and the leading end 45 projecting downwardly beyond the outer guide portion 28 in the pre-injection stage as shown in FIG. 7. The carpule assembly 60 has a tube 62 of uniform diameter conforming to the inner diameter of the barrel 12, and the tube 62 is closed at opposite ends by generally cylindrical plugs 63 and 64 to form a fluid chamber within the carpule assembly for the medication to be injected. The plugs 63 and 64 are basically of corresponding size and shape and each having axially spaced convex annular ridges 65 and 66. The fluid expelling plug member 63 is secured to the end of the plunger by a spire point 68 extending centrally for a limited distance into the plug 63. A plurality of sharp, rigid barbs 70 composed of plastic or other non-metallic material are mounted in spaced circumferential relation to one another at the end of the plug member 63 facing the plug so that when advanced through the fluid chamber in the carpule will move into engagement at the end of the plunger stroke with the needle-retaining member 64. Again, the barbs 70 penetrate the facing end of the plug member 64 so as to anchor or join the plug members 63 and 64 together. As in the first embodiment, the needle assembly 42 has a collar 46 which extends into a counterbore in the plug 64 and a sharpened needle end 44 extends upwardly through the plug 64 to communicate with the liquid-filled chamber. In this way, the spire point 68 is not required to effect positive engagement with the plug 64, as best seen from FIG. 8.

In use, the procedure or method followed is the same as described in the first embodiment in the successive steps of injecting a medical solution into a patient, retracting the needle into the carpule assembly, removing a portion of the guide assembly at the end of the syringe after injection and extending the needle through the guide once again to permit destruction of the end of the needle followed by retracting the remainder of the needle back into the carpule and disposing of the carpule.

Although the embodiments have been described in connection with a dental syringe, it will be appreciated that it has useful application for other types of hypodermic syringes and for virtually any gauge needle. Accordingly, while different embodiments have been herein set forth and described, other modifications and changes may be made without departing from the objects and features herein described and as further described by the appended claims.

I claim:

1. A syringe having a cylinder and plunger slidable therethrough, a carpule defining a fluid chamber for medication removably positioned in said cylinder having a retractable needle at a trailing end of said carpule for extension between a retracted position within said carpule and an extended position beyond a leading end of said syringe; a fluid-expelling first plug member at a trailing end of said carpule and a needle-retaining second plug member at a leading end of said carpule for extension of a trailing end of said needle through said second plug member into communication with a medical solution in said carpule between said first and second plug members, and a generally funnel-shaped guide member at said leading end of said syringe for guiding advancement of said needle between said retracted and extended positions; and wherein said needle includes an enlarged collar portion between said trailing end and said leading end of said needle for extension through a generally funnel-shaped bore of said funnel-shaped guide member and extension of said leading end of said needle through a central bore in a second portion of said guide member which is of reduced diameter relative to said funnel-shaped bore.

2. The syringe according to claim 1 wherein said second portion is threadedly connected to said guide member.

3. A dental syringe having an elongated hollow cylinder and a plunger normally positioned at a trailing end of said cylinder, a carpule removably positioned within said cylinder having a retractable needle at a trailing end of said carpule for extension through a leading end of said cylinder, a fluid-expelling first plug member at a trailing end of said carpule and a needle-retaining second plug member at a leading end of said carpule for extension of a trailing end of said needle through said second plug member into communication with a medical solution in said carpule between said first and second plug members, an opposite leading end of said needle extending through said leading end of said cylinder, and a generally funnel-shaped guide member at said opposite end of said cylinder for guiding said leading end of said needle repetitively through said leading end of said cylinder to successively inject said medical solution into a patient followed by severance and destruction of said leading end of said needle whereby to prevent reuse of the remainder of said needle; and wherein said needle includes an enlarged collar portion between said trailing end and said leading end of said needle for extension through a generally funnel-shaped bore of said funnel-shaped guide member and extension of said leading end of said needle through a central bore in a second portion of said guide member which is of reduced diameter relative to said funnel-shaped bore.

4. The syringe according to claim 3 wherein said second guide portion is removable from said first guide portion to expose said leading end of said needle extending beyond said collar for removal and destruction.

5. The syringe according to claim 3 wherein said fluid-expelling first plug member is slidable through said carpule in response to advancement of said plunger whereby to force said medical solution through said needle.

6. The syringe according to claim 3 wherein said fluid-expelling first plug member has barbed extensions at its leading end for positive engagement with said second plug member whereupon movement into engagement with said second plug member will retract said second plug member and said needle assembly through said carpule in response to retraction of said plunger.

7. The syringe according to claim 3 wherein said barbed extension is disposed in offset relation to said needle so as not to engage said needle when it penetrates said second plug member.

8. The syringe according to claim 1 wherein said first and second plug members are provided with annularly extending convex ridges in axially spaced relation to one another and in sealed relation to said carpule.

9. The syringe according to claim 1 wherein said second guide portion is removable from a first guide portion to expose said leading end of said needle extending beyond said collar for removal and destruction.

* * * * *